United States Patent [19]

Eisenbrand

[11] 4,150,146

[45] Apr. 17, 1979

[54] PROCESS FOR THE PREPARATION OF UNSYMMETRICALLY 1,3-DISUBSTITUTED NITROSO UREAS

[76] Inventor: Gerhard Eisenbrand, Banngartenstrasse 19, 6902 Sandhausen, Fed. Rep. of Germany

[21] Appl. No.: 800,452

[22] Filed: May 25, 1977

[30] Foreign Application Priority Data

May 25, 1976 [DE] Fed. Rep. of Germany ....... 2623420

[51] Int. Cl.$^2$ .............................................. A61K 31/17
[52] U.S. Cl. .................... 424/322; 260/349; 260/456 A; 260/553 R; 560/24
[58] Field of Search ....................... 260/553 R, 456 A; 424/322; 560/24

[56] References Cited

PUBLICATIONS

Eisenbrand et al., Z. Krebsforch, Klin. Onkol., 1976, 86 (3), pp. 279–286 (Eng.), Chemical Abstracts vol. 85, Abst. 85: 159,373a (1976).
Johnston et al., J. Med. Chem. vol. 9, pp. 892–911 (1966).
Garrett et al., J. Pharm. Sci., vol. 55, pp. 702–710 (1966).
Garrett et al., Chem. Abst. vol. 65, col. 7035 (1966).

*Primary Examiner*—John D. Randolph
*Attorney, Agent, or Firm*—Michael Klotz

[57] ABSTRACT

The invention relates to the preparation of unsymmetrically 1,3-disubstituted nitroso ureas from the corresponding N-substituted alkyl-N-nitrosocarbamoyl azide which is reacted with an amine, a diamine, an aminoalcohol, an aminoacid or an aminoacid derivative. The N-nitrosocarbamoyl azide is obtained by reacting the corresponding alkylcarbamoyl azide with nitrogen tetroxide in the cold. The alkylcarbamoyl azide is obtained by reacting the corresponding isocyanate with an alkali metal azide.

The invention further relates to novel nitroso ureas obtained thereby, to novel N-substituted alkyl-N-nitrosocarbamoyl azides, and to novel therapeutic compositions containing, as the active ingredient, the novel nitroso ureas.

13 Claims, No Drawings

PROCESS FOR THE PREPARATION OF UNSYMMETRICALLY 1,3-DISUBSTITUTED NITROSO UREAS

The present invention relates to a new process for the preparation of unsymmetrically 1,3-disubstituted nitroso ureas, its esters and salts, to novel unsymmetrically 1,3-disubstituted nitroso ureas, its esters and salts prepared thereby and to new intermediate compounds for their preparation.

Specific 1-(2-chloroethyl)-1-niroso ureas, particularly 1,3-bis-(2-chloroethyl)-1-nitroso urea (BCNU), have been used as chemotherapeutic agent for the treatment of a number of experimental and clinical tumors (Adv. in Cancer Res., 16, 237 to 332, 1972). A number of studies have been made of the working mechanism and the chemotherapeutic activity of such compounds, leading to the conclusion that the observed toxicity of the compounds is probably mostly influenced by the carbamoylating activity of the decomposition products (Wheeler et al., Cancer Res., 34, 194 to 200, 1974). However, the biological effects of the alkylating and carbamoylating agents, obtained by the breakdown of the nucleus in vivo and in vitro, are little known.

There is therefore the greatest need to prepare the analogs of the known nitroso ureas in order to modify their chemotherapeutic activity, particularly the toxicity and the anti-tumor activity, as well as their solubility in water or in tissue fluids.

It is an object of the invention to discover a new method for the preparation of unsymmetrically 1,3-disubstituted nitroso ureas which would also make possible the preparation of new analogs of BCNU.

It is a further object of the invention to discover new analogs of BCNU.

It is a further object of the invention to discover novel intermediate compounds from which the new analogs of BCNU can be prepared.

These and other objects of the invention are achieved by the discovery of a new method for the preparation of 1,3-disubstituted nitroso ureas, in which these compounds are prepared by the selective nitrosation of the corresponding carbamoyl azide which is then reacted with a suitable amino compound.

These objects are further achieved by the discovery of new analogs of BCNU which can now be prepared and which have improved properties when administered alone or in combination with other agents.

These objects are further achieved by the discovery of novel N-substituted alkyl-N-nitrosocarbamoyl azides from which the new unsymmetrially 1,3-disubstituted nitroso ureas can be made.

In the preparation of an unsymmetrical 1,3-disubstituted-nitroso urea, the selective nitrosation of a specified nitrogen atom of the urea is of utmost importance, for example, in the case of an unsymmetrically substituted homolog of BCNU, the nitrosation of the nitrogen atom which carries the 2-chloroethyl group. Studies of nitrosation in undiluted formic acid (JOhnson et al, J. Med. Chem. 9, 892 to 911, 1966) have shown that the formation of 1-(2-chloroethyl)-1-nitroso urea is favored only in those cases where the geometry of the substituent in the 3- position provides steric control and directs the nitroso group into the desired position. The selective nitrosation fails when this steric control is not present.

I have now surprisingly found that the selective nitrosation can be achieved simply and completely, if an N-substituted alkyl-N-nitrosocarbamoyl azide, desirably an N-haloalkyl-N-nitroso carbamoyl azide, is used for the preparation of disubstituted nitroso ureas. Particularly useful are N-(2-haloethyl)-N-nitrosocarbamoyl azides, preferably N-(2-chloroethyl)-N-nitrosocarbamoyl azide, advantageously the 2-fluoroethyl, 2-bromoethyl and 2-iodoethyl compounds.

My invention therefore, in accordance with one aspect thereof, is concerned with a process for the preparation of 1,3-disubstituted nitroso ureas in which an N-substituted alkyl-N-nitrosocarbamoyl azide is reacted, preferably at about 0° C., with an amine, a diamine, an aminoalcohol, an aminoacid or an aminoacid derivative to form the 1,3-disubstituted nitroso urea, the reaction being carried out in a solvent which is inert to the reactants under the reaction conditions. In the above alkyl compounds, the alkyl group may have from two to six carbon atoms and may be straight chained or branched or may be an unsubstituted cycloalkyl group or a cycloalkyl group substituted with an alkyl group having from one to four carbon atoms.

The hydrocarbon portion of the above amino compounds is an alkyl group, preferably having from two to six carbon atoms, advantageously from two to four carbon atoms, a cycloalkyl group, especially a cyclohexyl group, a cycloalkyl group substituted with an alkyl group, preferably having from one to four carbon atoms, or with one or more hydroxyl, halo or nitro groups, an unsubstituted phenyl, biphenyl or naphthyl group, or a phenyl, biphenyl or naphthyl group substituted with one or more lower alkyl, hydroxyl, halo or nitro groups. The aminoacid derivative may be an aminoacid ester or an aminoacid amide.

In accordance with another aspect of the invention, my invention is concerned with a process for the preparation of N-substituted alkyl-N-nitrosocarbamoyl azides by reacting the corresponding alkylcarbamoyl azide with nitrogen tetroxide in the cold, preferably at 0° C., in which the alkyl group of the alkyl compounds is defined as above. The preferred alkylcarbamoyl azide is a haloalkylcarbamoyl azide, particularly the 2-chloroalkyl and the 2-fluoroalkyl compounds, most particularly the 2-chloroethyl and the 2-fluoroethyl compounds.

In accordance with another aspect of the invention, the alkylcarbamoyl azide is prepared in one step and without the use of pyridine by reacting the corresponding isocyanate with an alkali metal azide, particularly sodium azide, especially activated sodium azide, preferably at about 0° C.

In accordance with the preferred aspect of the invention, my invention is concerned with the process for the preparation of unsymmetrically 1,3-disubstituted nitroso ureas by reacting an isocyanate with an alkali metal azide to form an alkylcarbamoyl azide, the reaction being carried out in an inert solvent, preferably with the addition of hydrochloric acid, reacting the alkylcarbamoyl azide with nitrogen tetroxide in the cold to form an N-alkyl-N-nitrosocarbamoyl azide, the reaction being preferably carried out at 0° C., and reacting the N-alkyl-N-nitrosocarbamoyl azide with an amino compound selected from the group consisting of amines, diamines, aminoalcohols, aminoacids and amino acid derivatives to form an unsymmetrically 1,3-disubstituted nitroso urea or an ester thereof, the reaction being carried out in a solvent which is inert to the reactants under the reaction conditions, the alkyl group of the alkyl compounds and the hydrocarbon portion of the amino compounds being defined as above.

The unsymmetrically 1,3-disubstituted nitroso ureas are converted to its esters or salts by methods well known in the art. The esters may also be obtained directly by the above process, if the amino compound used is an aminoacid ester or an aminoacid amide.

The process of the invention makes it possible to prepare a large number of unsymmetrically 1,3-disubstituted nitroso ureas and nitroso ureido compounds, which could not hitherto be prepared by methods known in the art or could only be prepared with a very inferior yield. It is therefore preferable to the process known from Helv. Chim. Acta, vol. 52, fasc. 8, 1969 and vol. 57, fasc. 8, 1974, No. 289 which prepares first the chloride and then the azide and must make use of pyridine, and to other conventional processes in which the urea structure is first obtained and is then nitrosated.

The N-nitrosation of the alkylcarbamoyl azides, for example the 2-chloroethylcarbamoyl azide, has proved that the nitroso group is attached in the required position. The subsequent aminolysis of the nitosated carbamoylating agent gives alkyl-N-nitrosoureas, for example the 2-chloroethyl-N-nitroso urea, which are free of isomers.

In accordance with a further aspect of the invention, my invention concerns the preparation of novel compounds of the formula:

R—NH CO N (NO) CH₂—CH₂—Cl and esters thereof, wherein (1) R is an alkyl group of from two to six carbon atoms, which may be substituted with one or more —OH, O—CO—R' or O—SO₂—R' groups, wherein R' is an organic group, (2) R is an alkyl group of from two to five carbon atoms and substituted with one or more —COOH, —COOR', —CONH₂ or —COOMe groups, wherein Me is a metal and R' is an organic group, and may be additionally substituted with one or more —OH, O—CO—R' or O—SO₂—R' groups, or (3) R is phenyl, biphenyl or naphthyl which may be substituted as in (1) or (2) and additionally with one or more alkyl group of one to four carbon atoms, and wherein in (1), (2) or (3) R may also be substituted with a further —NH CO N (NO) CH₂CH₂Cl residue.

The above compounds are stable, except in the presence of certain bases, and may be converted easily into its derivatives such as salts or esters, if the compound is not an ester. If a basic functional group is attached to the molecule, such as an —NH₂ group, it may be protected by converting it to a quaternary ammonium compound to avoid decomposition in the reaction and subsequently removing the quarternizing group.

In accordance with a further aspect of the invention, my invention concerns the preparation of novel N-haloalkyl-N-nitrosocarbamoyl azides, particularly N-chloroalkyl- and 2-fluoroalkyl-N-nitrosocarbamoyl azides, most particularly the N-(2-chloroethyl)-N-nitrosocarbamoyl azide.

In accordance with a further aspect of the invention, my invention concerns therapeutic compositions containing, as the active ingredient, the novel unsymmetrically 1,3-disubstituted nitroso urea, with or without other active ingredients.

It has been found that certain unsymmetrically 1,3-disubstituted nitroso ureas analogs of BCNU, of the above formula, show higher anti-tumor activity, alone or in combination with other compounds, while possessing improved solubility in water or in tissue fluids. It is also believed that certain new analogs of BCNU, of the above formula, have a lesser delayed toxicity than BCNU.

It is a particular advantage of the present invention that the process of the invention makes it possible to prepare nitroso urea compounds of the desired solubility. For example, the introduction of a hydrophylic group in the last step of the process in accordance with one aspect of the invention can produce a compound which acts rapidly and strongly after its application to the animal body. Such rapidly and strongly acting compound can be administered together with a compound having longer-lasting but lower activity in the animal body, which could not be applied with advantage alone as its low solubility would preclude sufficient concentration in the body. Compounds produced by the process of the invention can thus be applied to advantage also in combination with other compounds, particularly the less active compounds which are often also less toxic.

The compounds of the invention prove therefore their utility not only when applied to the animal body alone, but also when applied in combination with other compounds, particularly those which have not been of value when applied alone. The compounds of the invention can also be be combined with compounds such as Adriamycin, Cyclophosphamide, Busulfan or Methothrexat.

The invention will now be described by way of example with reference to the N-(2-chloroethyl)-N-nitrosocarbamoyl compound to illustrate the use in the synthesis of various Haloalkyl compounds. However, the invention is not to be limited thereby except as defined in the attached claims. The chemical compounds and the solvents used in the Examples were of synthesis grade or chemically pure. Nitrogen tetroxide was used in the form available in the trade, obtained from BASF, Ludwigshafen, Germany.

EXAMPLE 1

Preparation of 2-chloroethylcarbamoyl azide (I)

A solution of 2-chloroethyl isocyanate (0.2 mole) in 100 ml of benzene was slowly added to a stirred solution of activated sodium azide (0.2 mole) in 100 ml of hydrochloric acid (13%) maintained at 0° C. The two-phase reaction mixture was stirred for 4 hours at 0° C. and the water phase was removed. 2-chloroethylcarbamoyl azide was crystallized from benzene/petroleum ether in the form of white needles. Yield: 88%. M.P. 49.6 to 50.2° C. NMR(CDCl₃-TMS)δ=3.4 to 3.9 ppm (unres., 4H, CH²—CH²Cl); 6.12 ppm (br, s, iH, NH); MS(14 v):m/e 148(M+), m/e 106(M—N₃)+, m/e 105 (M—HN₃)+ =base peak. An intensity ratio of m/e 148 / m/e 150 is typical for a monochlorinated compound.

EXAMPLE 2

Preparation of N-(2-chloroethyl)-N-nitrosocarbamoyl azide (II)

Nitrogen tetroxide (0,3 mole) was slowly added to a suspension of anhydrous sodium acetate (0.6 mole) in 300 ml of carbon tetrachloride at −10° C. After warming to 0° C., 2-chloroethylcarbamoyl azide (0.2) was slowly added with a spatula to the stirred suspension. A white precipitate was formed (AcOH). After 15 minutes, the reaction mixture was poured into ice water.

The separated organic phase was extracted twice with 50 ml of a cold solution of NaHCO$_3$ (1 molar) and was then washed neutral with 2×50 ml of ice cold water saturated with NaCl. It was then dried over anhydrous sodium sulfate. No attempt was made to isolate N-(chloroethyl)-N-nitrosocarbamoyl azide as it is potentially explosive. The NMR spectroscopic examination of the CCl$_4$ solution (internal standard TMS) showed the complete absence of an NH— signal and showed a pattern which is typical for the A$_2$B$_2$ system of the nitrosated 2-chloroethylamino group. $\delta$=3.50 ppm (t, 2H, —CH$_2$—N—NO); 4.15 ppm (t, 2H, Cl—CH$_2$—).

The solution should be stored as cold as possible, for example deep-freezed, as it turns out that on standing at room temperature the Upfield pseudotriplet appears, having the center at $\delta$=4.87 ppm. While I do not wish to bound by this theory, I believe that the spectral change, which in one case took 48 hours, may possibly be ascribed to a thermally induced rearrangement of the compound, which possibly leads through the migration of the 1,3-acyl to the diazoester of azidocarbonic acid. If the solution is maintained at $-30°$ C., no such phenomenon takes place.

The reaction described in Examples 1 and 2 can also be carried out with the corresponding 2-fluoro, 2-bromo or 2-iodo compounds.

The following Examples show the use of N-(2-chloroethyl)-N-nitrosocarbamoyl azide for the preparation of various disubstituted 2-nitroso ureas.

EXAMPLE 3

Preparation of 1,1'-(polymethylene)-bis-3-(2-chloroethyl)-3-nitroso ureas (Compounds 1 to 5 of Table I)

Some 0.2 mole of N-(2-chloroethyl)-N-nitrosocarbamoyl azide in CCl$_4$ was diluted with an equal volume (150 ml) of cold (0° C.) n-pentane. (The yield of N-nitrosocarbamoyl azide from the nitrosation of the carbamoyl azide was taken as quantitative). Ethylene diamine (0.2 mole), dissolved in cold CCl$_4$/n-pentane was added dropwise to the stirred solution in an ice bath. After 3 hours, the the yellow precipitate formed was removed by suction and washed several times with benzene/pentane (1:1). It was then dissolved in acetone and the acetone solution poured into a tenfold volume of ice cold 0.1 N H$_2$SO$_4$. The precipitate was filtered off and again dissolved in acetone. The acetone solution was poured into a tenfold volume of water and the precipitate obtained again filtered off. This procedure was repeated until the wash water was neutral. After drying in a vacuum dessicator over CaCl$_2$, the nitroso urea was crystallized from methyl formate/isopropanol (1:1).

The process of this Example was repeated substituting ethylene diamine by propylene diamine to prepare Compound 2 of Table I, by tetramethylene diamine to prepare Compound 3, by pentamethylene diamine to prepare Compound 4, and by hexamethylene diamine to prepare Compound 5. The physical data for Compounds 1 to 5 are given in Table I.

EXAMPLE 4

Preparation of 1-($\omega$-hydroxyalkyl)-3-(chloroethyl)-3-nitroso ureas (Compounds 6 to 8 of Table I)

A solution of some 0.2 mole of N-(chloroethyl)-N-nitrosocarbamoyl azide in CCl$_4$ was diluted with 100 ml of cold isopropanol and the CCl$_4$ was removed under vacuum at 0° C. Thereafter, 0.3 mole of $\beta$-aminoethanol, dissolved in 50 ml of isopropanol, was added dropwise to the isopropanol solution at $-5°$ C. while stirring. The reaction was allowed to proceed until no unreacted N-(2-chloroethyl)-N-nitrosocarbamoyl azide could be detected by TLC. This required 4 hours for 1-(2-hydroxyethyl)-3-(2-chloroethyl)-3-nitroso urea (Compound 6). When the reaction was completed, an equal volume of cold 1 N H$_2$SO$_4$ was added and the acid solution was extracted with ethyl formate. The ethyl formate phase was washed neutral with water and the washings were re-extracted. The combined organic phases were dried over Na$_2$SO$_4$ and concentrated. The pure Compound 6 was crystallized in the form of light yellow needles from ethyl formate/n-pentane in a deep-freezer and then dried under vacuum.

The process of this Example was repeated substituting $\beta$-aminoethanol by $\gamma$-aminopropanol to prepare Compound 7, and by $\delta$-amino-n-butanol to prepare Coumpound 8. The reaction to prepare Compound 7 took 12 hours to completion. Compounds 7 and 8 could not be crystallized. They were purified by column chromatography on silica gel (solvent composition: acetone/n-pentane/benzene 1:1:1). After the removal of the solvent at 0° C. under vacuum, these liquid nitroso ureas were freeze dried at $-10°$ C. (24 hours).

The following Example illustrates the preparation of esters of 1-($\omega$-hydroxyalkyl-3-(2-chloroethyl)-3-nitroso ureas.

EXAMPLE 5

Preparation of a methanesulfonic acid ester of 1-(2-hydroxyethyl)-3-nitroso urea (Compound 9 of Table I)

0.06 mole of 1-(2-hydroxyethyl)-3-(2-chloroethyl)-3-nitroso urea was dissolved in 50 ml of pyridine, freshly distilled over KOH. 0.13 mole of methanesulfonyl chloride in 40 ml of pyridine was then added dropwise over 3 hours. The reaction charge was then left overnight at 0° C. 60 ml of ice water was then added with cooling, the temperature brought down to $-10°$ C. and the mixture was slowly acidified with concentrated HCl. It was then shaken with ethyl formate, the ethyl formate was dried over Na$_2$SO$_4$, concentrated and an equal volume of n-pentane was added. The methanesulfonic acid ester crystallized in a deep freezer at $-18°$ C. and was recrystallized from ethyl formate/n-pentane. The substance was shown by TLC to be pure; the results of the elementary analysis were within ±0.4% of theory. Molar absorption in the UV region, typical infrared absorptions and the NMR spectrum confirmed the purity and the structure. Yield: 73%; MP: 59°–61° C.

This compound is of special interest as it is built of the molecule halves of two cytostatically active substances, viz. BCNU and 1,4-bis-(methanesulfonyloxy)-butane of the formula (CH$_3$—SO$_2$—O—CH$_2$—CH$_2$)$_2$ ("Myleran")

Animal test results have shown excellent activity against rat autochthonic DMBA-induced mammary carcinoma, significantly exceeding that of "Adriamycin" (Reg. TM) which is a much used chemotherapeutic agent.

The following Example illustrates the preparation of a 3-nitrosoureido aminoacid amide by reacting an N-(substituted alkyl) N-nitrosocarbamoyl azide with an aminoacid amide.

EXAMPLE 6

Preparation of 2-(3-(2-chloroethyl))-3-nitrosoureido acetamide (Compound 10 of Table I)

A solution of 0.3 mole of glycinamide hydrochloride was brought to pH 9 with KOH and was added dropwise to an ice cold stirred solution of 0.2 mole of N-(2-chloroethyl)-N-nitrosocarbamoyl azide in 150 ml of isopropanol. The reaction proceeded quickly (in about 1 hour). When TLC showed no unreacted N-(2-chloroethyl)-N-nitrosocarbamoyl azide, it was acidified with 1 N $H_2SO_4$ and extracted with ethyl formate. The organic phase was washed neutral and dried over $Na_2SO_4$. The nitrosoureido compound was separated from its impurities by several fractional crystallizations from ethyl formate and was finally recrystallized from ethanol. TLC showed the substance to be pure. The NMR spectrum and the elementary analysis showed the presence of a half molecule of water of crystallization. UV and infrared spectroscopy confirmed the purity and the structure. Yield: 40%; MP (0° C.):114.2°–114.5° C.

Preliminary animal test results have shown that the above prepared Compound 10 has the same activity against s.c. Walker carcinosarcoma as BCNU. However, it is easier to apply than BCNU because of its better solubility in water. As well as that, and contrary to BCNU, it appears to have little delayed toxicity. Compound 10 also shows better activity than "Adriamycin" or BCNU against autochthonic DMBA-induced mammary rat carcinoma.

When glycine is used in the above preparation in place of glycinamide hydrochloride, 2(3-(2-chloroethyl))-3-nitrosoureido acetic acid is obtained, which may then be converted into its salt, particularly an alkali metal salt.

When a glycine ester is used in the above preparation in place of glycinamide hydrochloride, the reaction leads to the preparation of the corresponding 2-(3-(2-chloroethyl))-3-nitrosoureido acetic acid ester.

The sequence of chemical reaction steps in the preparation of Compounds 1 to 10 can be shown schematically as follows:

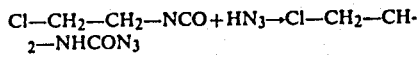  (I)

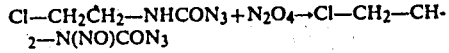  (II)

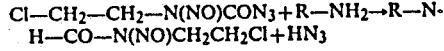  (III)

For Compounds 1 to 5, R represents the polymethylene group of 2 to 6 carbon atoms. For Compounds 6 to 7, R represents the ω-hydroxyalkyl residue of 2 to 4 carbon atoms. For Compound 9, R represents a 2-methanesulfonyloxyethyl residue and for Compound 10 an acetamide residue. Physical data for Compounds 1 to 10 are given in the accompanying Table I.

All the compounds synthesized were found by thin leaf chromatography (TLC) (silica gel leaves, solvents acetone/n-pentane benzene 1:1:1) to be pure.

The results of the elementary analysis were within ±0.4% of theory, with the exception of the liquid compounds 7 and 8 which were not stable enough for elementary analysis. However, also for these compounds the molar absorption in the UV region and the typical infrared absorption of the N-nitrosoureido group were in agreement with data known for other N-mitroso ureas. Also the NMR spectrum confirmed the structure and the purity of the compounds.

The chemotherapeutic activity of Compounds 1 to 8 against rat leukaemia L 5222 and s.c. Walker carcinosarcoma is shown in the accompanying Table II, together with that of still another BCNU analog and of BCNU itself. Compound 6 is shown to have outstanding activity.

Numerous modifications and variations of my invention are possible in the light of the above teachings and, therefore, within the scope of the appended claims, my invention may be practised other than as particularly described.

TABLE I

Physical properties of 2-chloroethyl-N-nitroso ureas

| Compound (CNU is 3-(2-chloroethyl)-3-nitroso urea of the formula —NHCON(NO)$CH_2CH_2Cl$) | Mp (° C.) $n_D^{20}$ | Yield (%) |
|---|---|---|
| 1. 1,1'-ethylenebis-CNU—$(CH_2)_2$—CNU | 129.9°–130.9° (dec.) | 35 |
| 2. 1,1'-propylenebis-CNU—$(CH_2)_3$—CNU | 69.2°–72.1° (dec.) | 35 |
| 3. 1,1'-tetramethylenebis-CNU—$(CH_2)_4$—CNU | 104.5°–106.1° (dec.) | 37 |
| 4. 1,1'-pentamethylenebis-CNU—$(CH_2)_5$—CNU | 96.0°–98.0° (dec.) | 39 |
| 5. 1,1'-hexamethylenebis-CNU—$(CH_2)_6$—CNU | 84.0°–86.0° (dec.) | 46 |
| 6. 1-(2-hydroxyethyl)-CNU—$CH_2$—$CH_2OH$ | 56.0°–58.0° (dec.) | 49 |
| 7. 1-(3-hydroxypropyl)-CNU—$(CH_2)_2$—$CH_2OH$ | $n_D^{20}$ = 1.4655 | 47 |
| 8. 1-(4-hydroxybutyl)-CNU—$(CH_2)_3$—$CH_2OH$ | $n_D^{20}$ = 1.4855 | 47 |
| 9. 1-(2-methanesulfonyloxy)ethyl)-3-(2-chloroethyl)-3-nitroso urea (CNU—$CH_2C$-$H_2OSO_2$—$CH_3$) | 59°–61° | 73 |
| 10. 2-(3-chloroethyl)-3-nitrosoureido acetamide | 114.2°–114.5° | 40 |

TABLE II

The chemotherapeutic activity of Compounds 1 to 8, another analog of BCNU, and BCNU against rat leukaemia L 5222 and s.c. Walker carcinosarcoma

| Compound[1] | L 5222[2] cures %[3] | s.c. Walker[4] T.W.I.%[5] |
|---|---|---|
| BCNU | 70 | 83 |
| 1 | 60 | 75 |
| 2 | 60 | 72 |
| 3 | 75 | 77 |
| 4 | 30 | 68 |
| 5 | 50 | 70 |
| 6 | 90 | 85 |
| 7 | 10 | 0 |
| 8 | 5 | 4 |
| 1,1'-(4-methyl-m-phenylene)bis-CNU | 0 | 35 |

[1] 50% of the acute $LD_{50}$ were given i.p.
[2] Treatment on day 6 after transplantation of 5 × 10⁶ cells.
[3] Rats surviving 60 days after treatment were considered cured.
[4] Treatment on day 4 after transplantation. Each group consisted of 10 Sprague Dawley rats.
[5] T.W.I. corresponds to tumor weight inhibition in % on day 8, calculated by the formula  × 100

What I claim is:
1. A compound of the formula:

R—NH CO N (NO) $CH_2$—$CH_2$—Cl wherein (1) R is an alkyl group of from two to six carbon atoms, which may be substituted with at least one —O—CO—R' or —O—SO$_2$—R' group wherein R' is lower alkyl, or R is a straight-chain alkyl group of from two to six carbon atoms, which may be substituted with at least one —OH group, or (2) R is an alkyl group of from two to six carbon atoms and substituted with a —COOH or —COOMe group or with one or more —COOR' or —CONH$_2$ groups, wherein Me is a metal and R' is lower alkyl, and may be additionally substituted with at least an —OH, —O—CO—R' or O—SO$_2$R' group, and wherein in (1) or (2) R may also be substituted with a further —NH CO N (NO) CH$_2$CH$_2$Cl residue.

2. An ester of the compound of claim 1.
3. A salt of the compound of claim 1.
4. 1-(2-hydroxyethyl)-3-(2-chloroethyl)-3-nitroso urea.
5. An ester of the compound of claim 4.
6. 1,1-'-tetramethylene-bis-3-(2-chloroethyl)-3-nitroso urea.
7. 1-(2-methanesulfonyloxyethyl)-3-(2-chloroethyl)-3-nitroso urea.
8. 2-(3-(2-chloroethyl)-3-nitrosoureido-acetamide.
9. 1,1'-(polyalkylene)-bis-3-(2-chloroethyl)-3-nitrosourea wherein the alkylene group has from two to six carbon atoms.
10. 1,1'-(polymethylene)-bis-3-(2-chloroethyl)-3-nitrosourea.
11. A therapeutic composition containing, as the active ingredient, the compound of claim 9.
12. A therapeutic composition containing, as the active ingredient, the compound of claim 1 together with a pharmaceutically acceptable carrier or auxiliary agent.
13. A therapeutic composition containing, as the active ingredient, the compound of claim 4 together with a pharmaceutically acceptable carrier or auxiliary agent.

* * * * *